(12) United States Patent
Soskic et al.

(10) Patent No.: US 7,998,970 B2
(45) Date of Patent: Aug. 16, 2011

(54) USE OF FINASTERIDE, DUTASTERIDE AND RELATED COMPOUNDS FOR THE PREVENTION OR TREATMENT OF NEUROLOGICALLY-ASSOCIATED DISORDERS

(75) Inventors: Vukic Soskic, London (GB); André Schrattenholz, Mainz (DE)

(73) Assignee: ProteoSys AG, Mainz (DE)

( * ) Notice: Subject to any disclaimer, the term of this patent is extended or adjusted under 35 U.S.C. 154(b) by 1110 days.

(21) Appl. No.: 11/720,650

(22) PCT Filed: Dec. 2, 2005

(86) PCT No.: PCT/EP2005/012925
§ 371 (c)(1),
(2), (4) Date: Jun. 1, 2007

(87) PCT Pub. No.: WO2006/058781
PCT Pub. Date: Jun. 8, 2006

(65) Prior Publication Data
US 2009/0170889 A1    Jul. 2, 2009

Related U.S. Application Data

(60) Provisional application No. 60/632,601, filed on Dec. 3, 2004.

(51) Int. Cl.
*A61K 31/473*    (2006.01)
*C07D 221/18*    (2006.01)
*C07K 14/47*    (2006.01)
*C12N 9/02*    (2006.01)

(52) U.S. Cl. ............ 514/284; 435/189; 530/350; 546/77

(58) Field of Classification Search .................. 514/284; 435/189; 530/350; 546/77
See application file for complete search history.

(56) References Cited

U.S. PATENT DOCUMENTS 5,565,467 A    10/1996    Batchelor et al.
2004/0198753 A1*  10/2004    Kase et al. ................. 514/263.2

FOREIGN PATENT DOCUMENTS

| EP | 0 155 096 A | 9/1985 |
|---|---|---|
| WO | WO 98/38210 A | 9/1998 |
| WO | WO 03/092588 A | 11/2003 |
| WO | WO 2004/016595 A | 2/2004 |

OTHER PUBLICATIONS

Reddy, "Testosterone modulation of seizure susceptibility is mediated by neurosteroids 3alpha-androstanediol and 17beta-estradiol", Neuroscience, vol. 129, No. 1, 2004, pp. 195-207.
Altomare et al., "Depression circumstantially related to the administration of finasteride for androgenetic alopecia", Journal of Dermatology, vol. 29, No. 10, Oct. 2002, pp. 665-669.

* cited by examiner

*Primary Examiner* — Jennifer M Kim
(74) *Attorney, Agent, or Firm* — Rothwell, Figg, Ernst & Manbeck, P.C.

(57) ABSTRACT

The present invention relates to new pharmaceutical uses of 4-azasteroid compounds, in particular of Finasteride/Dutasteride/Dutasteride and Dutasteride, particularly preferred of Finasteride/Dutasteride/Dutasteride, and its pharmaceutically acceptable derivatives, and combinations comprising said compounds. The invention also features generally the use of a modulator compound of neuroprotective conditions via beta subunits of shaker-type voltage-gated potassium channels and/or via members of solute carriers family 25, in particular Aralar (member 12) and adenine-nucleotide translocators 1 & 2 (member 4 & 5) and/or via a 4-nitrophenylphosphatase domain and non-neuronal SNAP25-like protein homolog 1 (NIPSNAP 1) as a neuroprotective medicament, particularly as a medicament for the prevention and/or treatment of neurological diseases such as dementia, Parkinson, Alzheimer, schizophrenia or epilepsy. The demonstrated inhibition of the MPTP appears to constitute a novel principle applicable to all pathological conditions which have underlying excitotoxic/mitochondrial mechanisms, like: amyotrophic lateral sclerosis, Alzheimer's disease, depression, epilepsy, multiple sclerosis, pain, Parkinson's disease, schizophrenia, traumatic brain and spinal chord injury, stroke and other ischemic conditions in the brain.

11 Claims, 9 Drawing Sheets

USE OF FINASTERIDE, DUTASTERIDE AND RELATED COMPOUNDS FOR THE PREVENTION OR TREATMENT OF NEUROLOGICALLY-ASSOCIATED DISORDERS

CROSS REFERENCE TO RELATED APPLICATION

This application is a 35 USC §371 National Phase Entry Application from PCT/EP2005/012925, filed Dec. 2, 2005, and designating the United States, which claims the benefit of U.S. Provisional 60/632,601, filed Dec. 3, 2004.

The present invention relates to new pharmaceutical uses of 4-azasteroid compounds, in particular of Finasteride and Dutasteride, preferably Dutasteride, and their pharmaceutically acceptable derivatives, and combinations comprising said compounds.

The invention also features generally the use of a modulator compound of neuroprotective conditions via beta subunits of shaker-type voltage-gated potassium channels and/or via members of solute carriers family 25, in particular Aralar (member 12) and adenine-nucleotide translocator (members 4 and 5) and/or via a 4-nitrophenylphosphatase domain and non-neuronal SNAP25-like protein homolog 1 (NIPSNAP 1) as a neuroprotective medicament, particularly as a medicament for the prevention and/or treatment of neurological diseases such as dementia, Parkinson, Alzheimer, schizophrenia, or epilepsy or resulting from stroke or trauma.

Finasteride, a synthetic 4-azasteroid compound, $5\alpha,17\beta$-N-(1,1-dimethylethyl)-3-oxo-4-azaandrost-1-ene-17-carboxamide, $17\beta$-(N-tert-butyl-carbamoyl)-4-aza-$5\alpha$-androst-7-en-3-one, is an inhibitor of $5\text{-}\alpha$-reductase, the enzyme which converts testosterone to the more potent androgen, $5\alpha$-dihydrotestosterone (DHT). It is known for use in treatment and/or prevention of benign prostatic hyperplasia and hair loss (Ashburn T T & Thor K B, 2004, Drug repositioning: identifying and developing new uses for existing drugs, Nature Reviews 3, 673-683). Further, U.S. Pat. No. 6,040,409 describes the use of Finasteride in the prevention and treatment of atherosclerosis, coronary artery heart disease, stroke and peripheral vascular disease in humans and animals. U.S. Pat. No. 6,174,892 discloses a method of treating acne with Finasteride.

Dutasteride, a synthetic 4-azasteroid compound, $5\alpha,17\beta$-N-[2,5-bis (trifluoromethyl)phenyl]-3-oxo-4-azaandrost-1-ene-17-carboxamide is also an inhibitor of $5\text{-}\alpha$-reductase. It is known for its use in the treatment of androgen responsive and mediated diseases (U.S. Pat. No. 5,565,467).

For the preparation, pharmacology, pharmacokinetics and mechanism of action of Finasteride and Dutasteride, the following references are referred to:

Preparation:
EP-A-0 155 096; U.S. Pat. No. 4,760,071; G. H. Rasmusson et al., J. Med. Chem. 29, 2298 (1986); A. Bhattacharya et al., J. Am. Chem. Soc. 110, 3318 (1988).

Inhibition of $5\alpha$-reductase in vitro: T. Liang et al., Endocrinology 117, 571 (1985).

Inhibition of $5\alpha$-reductase in vivo: J. R. Brooks et al., Steroids 47, I (1986).

HPLC determination in plasma and urine and preliminary pharmacokinetics: J. R. Carlin et al., J. Chromatog. 427, 79 (1988).

Effects on hair growth in stumptail macaques: L. Rhodes et al., J. Clin. Endocrinol. Metab. 79, 991 (1994).

Clinical pharmacology: J. Imperato-McGinley et al., V. Clin. Endocrinol. Metab. 70, 777 (1990); G. J. Gormley et al., V. Clin. Endocrinol. Metab. 70, 1136 (1990).

Clinical effects on hormone levels in male pattern baldness: A L Dallob et al., V. Clin. Endocrinol. Metab. 79, 703 (1994).

The shaker potassium channel beta subunit (AKR6) belongs to the aldo-keto reductases (AKRs) representing a growing oxidoreductase superfamily. Forty proteins have been identified and characterized as AKRs, and an additional fourteen genes may encode proteins related to the superfamily (http://www.med.upenn.edu/akr/). The largest family (AKR1) contains the aldose reductases, aldehyde reductases, and HSDs (Jez J M, Flynn T G, Penning T M. A new nomenclature for the aldo-keto reductase superfamily. Biochem Pharmacol. 1997 Sep. 15; 54(6):639-47; Hyndman D, Bauman D R, Heredia W, Penning T M. The aldo-keto reductase superfamily homepage. Chem Biol Interact. 2003 Feb. 1; 143-144:621-31). There are indications that the AKR6, the shaker beta-subunits, facilitate or regulate the binding of steroids to a variety of potassium channels (Valverde M A, Rojas P, Amigo J, Cosmelli D, Orio P, Bahamonde M I, Mann G E, Vergara C, Latorre R Acute activation of Maxi-K channels (hSlo) by estradiol binding to the beta subunit. Science. 1999 Sep. 17; 285(5435):1929-31; Korovkina V P, Brainard A M, Ismail P, Schmidt T J, England S K. Estradiol binding to maxi-K channels induces their down-regulation via proteasomal degradation. J Biol. Chem. 2004 Jan. 9; 279(2):1217-23. Epub 2003 Oct. 10) and that this is the reason for various cytoprotective actions around regulation and/or modulation of potassium channel activities (Jamali K, Naylor B R, Kelly M J, Ronnekleiv O K. Effect of 17beta-estradiol on mRNA expression of large-conductance, voltage-dependent, and calcium-activated potassium channel alpha and beta subunits in guinea pig. Endocrine. 2003 April; 20(3):227-37).

Moreover, the Shaker family of voltage-gated $K^+$ channels plays a crucial role in the mitogenic response of T cells. There are indications that its function can be influenced by lipid-protein interactions and in particular by cholesterol, possibly again via the regulatory beta-subunits (Hajdu P, Varga Z, Pieri C, Panyi G, Gaspar R Jr Cholesterol modifies the gating of Kv1.3 in human T lymphocytes. Pflugers Arch. 2003 March; 445(6):674-82. Epub 2003 Jan 18). This implies sorting to specialized membrane compartments called "rafts", thought to be essential in neuronal signal transduction and pathology (Martens J R, Navarro-Polanco R, Coppock E A, Nishiyama A, Parshley L, Grobaski T D, Tamkun M M. Differential targeting of Shaker-like potassium channels to lipid rafts. J Biol. Chem. 2000 Mar. 17; 275(11):7443-6; Yang X L, Xiong W C, Mei L. Lipid rafts in neuregulin signaling at synapses. Life Sci. 2004 Oct. 8; 75(21):2495-504). Through their ability to interact with a range of alpha subunits, the beta subunits of voltage-gated K channels are likely to have a much broader impact on the signalling properties of neurons and muscle fibres than previously suggested (Wilson G F, Wang Z, Chouinard S W, Griffith L C, Ganetzky B. Interaction of the K channel beta subunit, Hyperkinetic, with eag family members. J Biol. Chem. 1998 Mar. 13; 273(11): 6389-94; Birnbaum S G, Varga A W, Yuan L L, Anderson A E, Sweatt J D, Schrader L A. Structure and function of Kv-4-family transient potassium channels. Physiol Rev. 2004 July; 84(3):803-33), even with implications in neurodegenerative diseases like Alzheimer's dementia (Pan Y, Xu X, Tong X, Wang X Messenger RNA and protein expression analysis of voltage-gated potassium channels in the brain of Abeta(25-35)-treated rats. J Neurosci Res. 2004 Jul. 1; 77(1):94-9).

It has now been found that the beta subunit of the shaker potassium channel (voltage-gated potassium channel beta 2 subunit; $K^+$ channel beta-2 subunit: Kv-beta-2) can be specifically enriched by using a Finasteride- or Dutasteride-derived affinity tag.

Aralar1 is an isoform of the mitochondrial carrier of aspartate-glutamate (AGC), a calcium regulated carrier, which is important in the malate-aspartate NADH shuttle. Aralar1 is the only isoform expressed in neurons and its levels undergo a marked increase during in vitro maturation, which is higher than the increase in mitochondrial DNA in the same time window. Aralar1 mRNA and protein are widely expressed throughout neuron-rich areas in adult mouse CNS with clear enrichments in sets of neuronal nuclei in the brainstem and, particularly, in the ventral horn of the spinal cord (Ramos M, del Arco A, Pardo B, Martinez-Serrano A, Martinez-Morales J R, Kobayashi K, Yasuda T, Bogonez E, Bovolenta P, Saheki T, Satrustegui J Developmental changes in the $Ca^{2+}$-regulated mitochondrial aspartate-glutamate carrier aralar1 in brain and prominent expression in the spinal cord. Brain Res Dev Brain Res. 2003 Jun. 12; 143(1):33-46).

The adenine nucleotide translocator 1 (Ant1) is an inner mitochondrial membrane protein involved with energy mobilization during oxidative phosphorylation. Adenine nucleotide translocator 1 is thought to be involved in a variety of protective mechanisms for cardiac and neuronal cells against ischemia and apoptosis (Ardehali H. Chen Z, Ko Y, Mejia-Alvarez R, Marban E. Multiprotein complex containing succinate dehydrogenase confers mitochondrial ATP-sensitive $K^+$ channel activity. Proc Natl Acad Sci USA. 2004 Aug. 10; 101(32):11880-5. Epub 2004 Jul. 29; Law A K, Gupta D, Levy S, Wallace D C, McKeon R J, Buck C R. TGF-beta1 induction of the adenine nucleotide translocator 1 in astrocytes occurs through Smads and Sp1 transcription factors. BMC Neurosci. 2004 Jan. 13; 5(1):1). Most importantly, the calcium-dependent Ant1 is essential constituent of the mitochondrial permeability transition pore (MPTP). The MPTP is an important proapoptotic protein complex in mitochondria. Although it is activated by many signals for apoptosis induction, the role of its various subunits in cell death induction has remained largely unknown. It has been shown that of its components, only the voltage-dependent anion channel (VDAC-1) in the outer mitochondrial membrane and the adenine nucleotide translocator-1 (ANT-1), a MPT-pore subunit of the inner membrane, are apoptosis inducers. (see e.g. following references: PMID 14729611: Schubert A, Grimm S., Cancer Res. 2004 Jan. 1; 64(1):85-93. Cyclophilin D, a component of the permeability transition-pore, is an apoptosis repressor; PMID 16108756: Solaini G, Harris D A. Biochemical dysfunction in heart mitochondria exposed to ischaemia and reperfusion. Biochem J. 2005 Sep. 1; 390(Pt 2):377-94; PMID 15807658: Saris N E, Carafoli E. A historical review of cellular calcium handling, with emphasis on mitochondria. Biochemistry (Mosc). 2005 February; 70(2): 187-94; PMID15573402: Sullivan P G, Rabchevsky A G, Waldmeier P C, Springer J E. Mitochondrial permeability transition in CNS trauma: cause or effect of neuronal cell death? J Neurosci Res. 2005 Jan 1-15; 79(1-2):231-9; PMID15539639: Crow M T, Mani K, Nam Y J, Kitsis R N. The mitochondrial death pathway and cardiac myocyte apoptosis. Circ Res. 2004 Nov. 12; 95 (10):957-70).

It has been found that the proteins Aralar1 (SLC25-12) and adenine nucleotide translocator 1 & 2 (SLC25-4 & 5) are bound by Finasteride/Dutasteride-related affinity tags.

The protein NIPSNAP1 has been described as a component of the postsynaptic density (PSD), a structure thought to be involved in synaptic plasticity and thus part of the molecular basis of learning and memory. NIPSNAP1 belongs to a group of proteins involved in activity-dependent dynamic changes (Satoh K, Takeuchi M, Oda Y, Deguchi-Tawarada M, Sakamoto Y, Matsubara K, Nagasu T, Takai Y. Identification of activity-regulated proteins in the postsynaptic density fraction. Genes Cells. 2002 February; 7(2):187-97). The NIPSNAP family has putative roles in vesicular trafficking and the formation of functional membrane domains, called lipid rafts (Buechler C, Bodzioch M, Bared S M, Sigruener A, Boettcher A, Lapicka-Bodzioch K, Aslanidis C, Duong C Q, Grandl M, Langmann T, Dembinska-Kiec A, Schmitz G. Expression pattern and raft association of NIPSNAP3 and NIPSNAP4, highly homologous proteins encoded by genes in close proximity to the ATP-binding cassette transporter A1. Genomics. 2004 June; 83(6):1116-24).

It has been found that the protein NIPSNAP1 is significantly enriched by a Finasteride- or Dutasteride-related affinity target.

The use of affinity targets in a functional cellular in vitro model of neuroprotection allows the screening for test compounds with novel neuroprotective modes of action.

Surprisingly, it was found that Finasteride, Dutasteride and related compounds have a previously unknown mode of action as ligands of the shaker potassium channel beta subunits and additionally to members of the solute carrier protein family (SLC 25), in particular Ant1 and the raft-associated protein NIPSNAP1. Due to these previously unknown neuroprotective effects, Finasteride, Dutasteride and related compounds are suitable as cytoprotective and particularly neuroprotective drugs and new lead structures for the development and optimization of new therapeutic compounds.

Further, the invention relates to the proteins Aralar1 (SLC 25-12), adenine nucleotide translocator 1 & 2 (SLC 25 4 & 5) and NIPSNAP1 as new cyto- and/or neuroprotective targets, generally for cytoprotection and, in particular, for the treatment of neurodegenerative disorders.

A further aspect of the invention is the use of NIPSNAP1 as a Finasteride- or Dutasteride-related marker and/or target.

Therefore, a first aspect of the present invention relates to the use of a compound of formula (I)

(I)

wherein $R^1$ and $R^2$ are independently of one another in each case hydrogen or methyl, $R^3$ is hydroxy,
  $C_1$-$C_8$-alkyl, $C_3$-$C_8$-cycloalkyl, $C_1$-$C_8$-alkoxy, $C_1$-$C_8$-mono- or dialkylamino or $C_1$-$C_8$-alkyldiamino, wherein each of the preceding residues can be unsubstituted or substituted by one to three substituents, independently of one another selected from the group consisting of hydroxy, halo, cyano, $C_1$-$C_4$-alkyl, $C_1$-$C_4$-alkoxy and phenyl,
  heteroaryl, heteroaryloxy, heteroarylamino, aryl, aryloxy or arylamino, wherein the heteroaryl or aryl moiety of each of the preceding residues can be unsubstituted or substituted by one to three substituents, independently of one another selected from the group consisting of hydroxy, halo, cyano, $C_1$-$C_4$-alkyl, $C_1$-$C_4$-alkoxy, trihalomethyl, phenyl and phenyloxy, $R^4$, $R^5$ and $R^6$ are independently of one another in each case hydrogen or $C_1$-$C_8$ alkyl, n is 0 or 1 and ⸺ is a double or a single bond, or of a salt or derivative thereof for the manufacture of a cytoprotective, particularly neuroprotective medicament.

The general terms used herein above and herein below preferably have the following meanings:

Halo or halogen is, for example, fluorine, chlorine, bromine or iodine.

Trihalomethyl is, for example, trifluoromethyl or trichloromethyl, particularly trifluoromethyl.

$C_1$-$C_8$-alkyl is, for example, methyl, ethyl, n-propyl, isopropyl, n-butyl, isobutyl, sec-butyl, tert-butyl, n-pentyl, neopentyl, n-hexyl, n-heptyl or n-octyl, preferably $C_1$-$C_4$-alkyl, especially methyl or ethyl, and more especially methyl.

$C_3$-$C_8$-cycloalkyl are monocyclic alkyl groups with 3 to 8 carbon ring members, eg. $C_3$-$C_8$-cycloalkyl such as cyclopropyl, cyclobutyl, cyclopentyl, cyclohexyl, cycloheptyl and cyclooctyl.

$C_1$-$C_8$-alkoxy are straight-chain or linear alkyl groups with 1 to 8, preferably 1 to 4 carbon atoms which are bound to the structure by an oxygen atom (—O—).

$C_1$-$C_8$-mono- or dialkylamino are straight-chain or branched alkyl groups with 1 to 8 carbon atoms, preferably with 1 to 4 carbon atoms, which are bound to the structure by an amino group (—NH—) or by the nitrogen atom (—N:) respectively.

$C_1$-$C_8$-alkyldiamino are straight-chain or branched alkyl groups with 1 to 8 carbon atoms, preferably with 1 to 4 carbon atoms, which are bound to the structure by one of the amino groups (—NH—), e.g. $H_2N$—$(CH_2)_2$—NH—.

Heteroaryl, heteroaryloxy and heteroarylamino are aromatic mono- or polycyclic radicals, which in addition to carbon ring members additionally can contain heteroatoms such as nitrogen, oxygen and/or sulfur, e.g. one to four nitrogen atoms or one to three nitrogen atoms and an oxygen or a sulfur atom or an oxygen and/or a sulfur atom and which are bonded to the structure directly or (heteroaryloxy), via an oxygen atom (—O—) or (heteroarylamino) via an amino group (—NH—).

Examples of heteroaryl, heteroaryloxy and heteroarylamino groups may be selected from:

5-membered heteroaryl, containing one to four nitrogen atoms or one to three nitrogen atoms and a sulfur or oxygen atom or an oxygen and/or a sulfur atom: 5-membered ring heteroaryl groups, which in addition to carbon atoms can contain one to four nitrogen atoms or one to three nitrogen atoms and a sulfur or oxygen atom or an oxygen and/or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

fused 5-membered heteroaryl, containing one to four nitrogen atoms or one to three nitrogen atoms and/or an oxygen or sulfur atom: 5-membered ring heteroaryl groups, which in addition to carbon atoms can contain one to four nitrogen atoms or one to three nitrogen atoms and a sulfur or oxygen atom or an oxygen and/or a sulfur atom as ring members, and in which two adjacent carbon ring members or a nitrogen and an adjacent carbon ring member can be bridged to form an aromatic or heteroaromatic bicycle or polycycle, eg. benzofuranyl, isobenzofuranyl, benzothienyl, isobenzothienyl, indolyl, isoindolyl, benzoisoxazolyl, benzoxazolyl, benzoisothiazolyl, benzothiazolyl, indazolyl, benzimidazolyl, pyrrolopyridinyl, pyrrolopyridazinyl, pyrrolopyrimidinyl, pyrrolopyrazinyl, pyrrolotriazinyl, furopyridinyl, furopyridazinyl, furopyrimidyl, furopyrazinyl, furotriazinyl, thienopyridinyl, thienopyridazinyl, thienopyrimidyl, thienopyrazinyl, thienotriazinyl, imidazopyridinyl, imidazopyridazinyl, imidazopyrimidyl, imidazopyrazinyl, imidazotriazinyl, pyrazolopyridinyl, pyrazolopyridazinyl, pyrazolopyrimidyl, pyrazolopyrazinyl, pyrazolotriazinyl, isoxazolopyridinyl, isoxazolopyridazinyl, isoxazolopyrimidyl, isoxazolopyrazinyl, isoxazolotriazinyl, oxazolopyridinyl, oxazolopyridazinyl, oxazolopyrimidyl, oxazolopyrazinyl, oxazolotriazinyl, isothiazolopyridinyl, isothiazolopyridazinyl, isothiazolopyrimidyl, isothiazolopyrazinyl, isothiazolotriazinyl, thiazolopyridinyl, thiazolopyridazinyl, thiazolopyrimidyl, thiazolopyrazinyl, thiazolotriazinyl, triazolopyridinyl, triazolopyridazinyl, triazolopyrimidyl, triazolopyrazinyl and triazolotriazinyl;

5-membered heteroaryl bonded via nitrogen, containing one to four nitrogen atoms, or benzo-fused 5-membered heteroaryl bonded via nitrogen, containing one to three nitrogen atoms: 5-membered ring heteroaryl groups, which in addition to carbon atoms can contain one to four nitrogen atoms or one to three nitrogen atoms as ring members, and in which two adjacent carbon ring members or a nitrogen and an adjacent carbon ring member can be bridged by a buta-1,3-diene-1,4-diyl group, these rings being bonded to the structure via one of the nitrogen ring members eg. 1-pyrrolyl, 1-imidazolyl, 1-pyrazolyl and 1,2,4-triazol-1-yl;

6-membered heteroaryl, containing one to three or one to four nitrogen atoms: 6-membered ring heteroaryl groups, which in addition to carbon atoms can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

fused 6-membered heteroaryl, containing one to four nitrogen atoms: 6-membered ring heteroaryl groups in which two adjacent carbon ring members can be bridged to form an aromatic or heteroaromatic biocycle or polycycle, eg. quinoline, isoquinoline, quinazoline and quinoxaline, or the corresponding oxy or amino groups.

Aryl are aromatic mono- or polycyclic carbon residues which are bound directly to the structure, e.g. phenyl, naphthyl, anthranyl, especially phenyl or naphthyl, and more especially phenyl.

Aryloxy are aromatic mono- or polycyclic carbon residues which are bound by an oxygen atom (—O—) to the structure, e.g. phenyloxy or naphthyloxy, preferably phenyloxy.

Arylamino are aromatic mono- or polycyclic hydrocarbon residues which are bound by an amino group (—NH—) to the structure, preferably phenylamino or naphthylamino.

The term "salt" preferably refers to pharmaceutically acceptable salts of compounds of formula (I) with suitable cations and/or anions. Examples of suitable cations are alkaline metal cations such as $Li^+$, $Na^+$ and $K^+$, alkaline earth metal cations such as $Mg^{2+}$ and $Ca^{2+}$ as well as suitable organic cations, e.g. ammoniums or substituted ammonium cations. Examples of pharmaceutically acceptable anions are inorganic aniones such as chloride, sulfate, hydrogen sulfate, phosphate or organic cations such as acetate, citrate, tartrate etc.

The invention relates preferably to the use of compounds of formula (I), wherein independently of each other $R^1$ is hydrogen or methyl, $R^2$ is methyl, $R^3$ is hydroxy, $C_1$-$C_8$-mono- or dialkylamino, $C_1$-$C_8$-alkyldiamino or arylamino, wherein the aryl moiety is substituted by one to three substituents, independently of one another selected from the group consisting of hydroxy, halo, cyano, $C_1$-$C_4$-alkyl, $C_1$-$C_4$-alkoxy or trihalomethyl, $R^4$ is hydrogen, α-methyl or β-methyl, $R^5$ is hydrogen or β-methyl,

$R^6$ is hydrogen, methyl or ethyl,
n is 0, and/or
═ is a double or single bond.

Preferred compounds of formula (I) that may be employed in the present invention include the following:
17β-(N-tert-butylcarbamoyl)-4-aza-5α-androst-1-en-3-one,
17β-(N-isobutylcarbamoyl)-4-aza-5α-androst-1-en-3-one,
17β-(N-tert-octylcarbamoyl)-4-aza-5α-androst-1-en-3-one,
17β-(N-octylcarbamoyl)-4-aza-5α-androst-1-en-3-one,
17β-(N-1,1-diethylbutylcarbamoyl)-4-aza-5α-androst-1-en-3-one,
17β-(N-neopentylcarbamoyl)-4-aza-5α-androst-1-en-3-one,
17β-(N-tert-amylcarbamoyl-4-aza-5α-androst-1-en-3-one,
17β-(N-tert-hexylcarbamoyl)-4-aza-5α-androst-1-en-3-one, and
5α, 17β-N-[2,5-bis(trifluoromethyl)phenyl]-3-oxo-4-azaandrost-1-ene-17-carboxamide
and the corresponding compounds wherein the 4-nitrogen is substituted in each of the above named compounds by a methyl or an ethyl radical.

Preferably preferred compounds of formula (I) that may be employed in the present invention are 17β-(N-tert-butylcarbamoyl)-4-aza-5α-androst-1-en-3-one, (Finasteride) and 5α,17β-N-[2,5-bis(trifluoromethyl)phenyl]-3-oxo-4-azaandrost-1-ene-17-carboxamide (Dutasteride).

The most preferred compound of formula (I) that may be employed in the present invention is 5α,17β-N-[2,5-bis(trifluoromethyl)phenyl]-3-oxo-4-azaandrost-1-ene-17-carboxamide (Dutasteride).

A further compound of formula (I) that may be employed in the present invention is

COAAA

4α,6α-di methyl-2-oxo-hexadecahydro-indeno[5,4-f]quinoline-7-carboxylic-acid [COAAA].

Another compound of formula (I) that may be employed in the present invention is

AEOAA

4α,6α-dimethyl-2-oxo-hexadecahydro-indeno[5,4-f]quinoline-7-carboxylic-(2-amino-ethyl)-amide hydrochloride [AEOAA].

Figure 1:
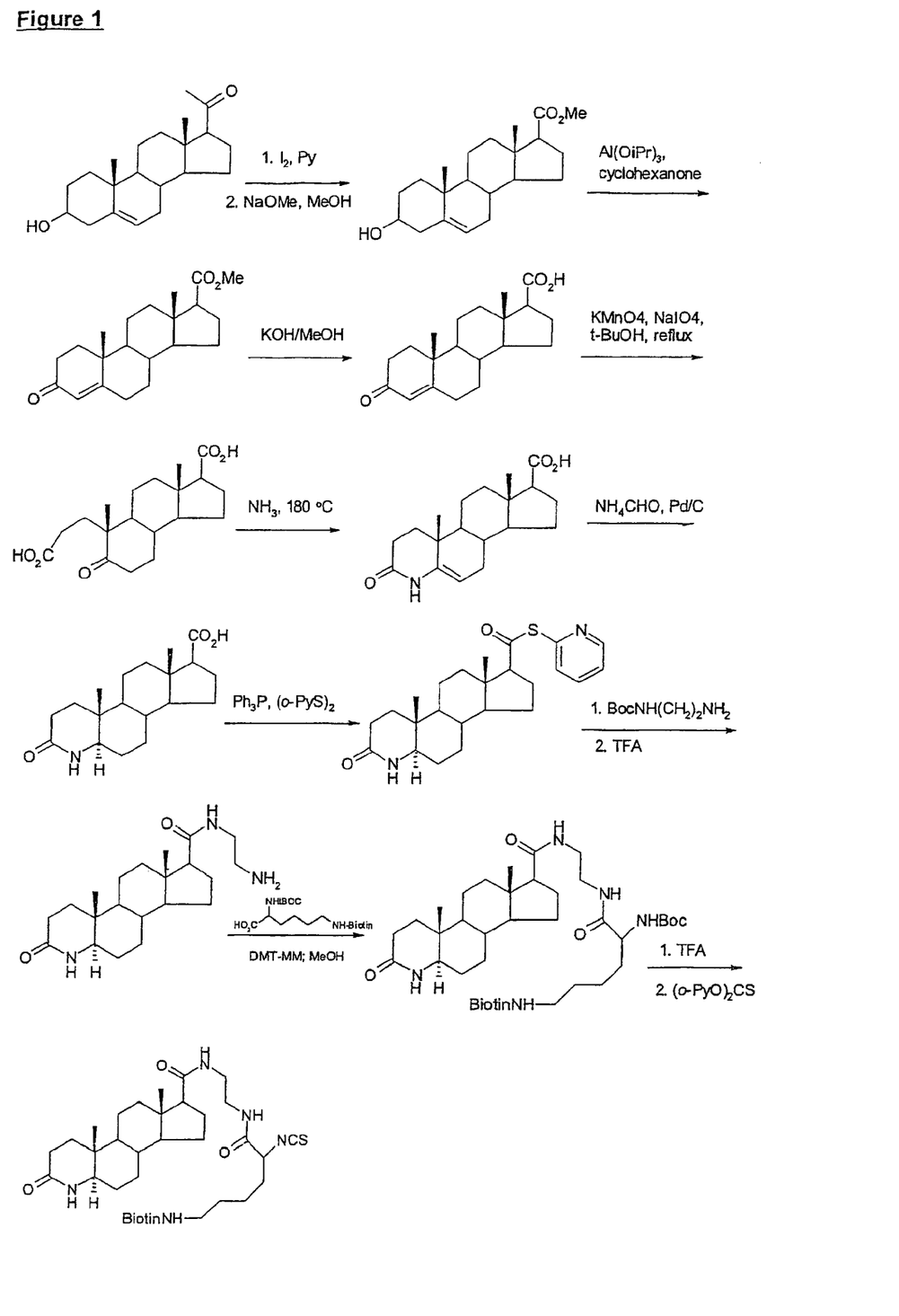
FIG. 1 describes a chemical proteomics tool to identify the neuronal Finasteride and Dutasteride binding site.

The compounds of formula (I) can be prepared according to procedures well-known in the art which are described in U.S. Pat. No. 4,760,071 and EP-A-0 155 096, for example or by analog preparation procedures. The preparation of Finasteride is described in U.S. Pat. No. 4,760,071. The preparation of Dutasteride is described in U.S. Pat. No. 5,565,467. The preparation of COMA and AEOAA is shown in FIG. 1.

The compound COMA is known from the literature (G. H. Rasmusson et al., J. Med. Chem. 27, 1690-1701 (1984)). The compound AEOAA is novel and a part of the invention.

The term "derivative" of compounds of formula (I) used herein means any molecules which are converted under physiological conditions to a compound of formula (I) or molecules which are products of metabolisation reactions of a compound of formula (I).

Preferably, compounds of formula (I) are used for the manufacture of a medicament for the prevention or treatment of neurologically-associated disorders. For example these disorders are neurodegenerative or neuroinflammatory conditions in disorders such as dementia, Parkinson, Alzheimer, schizophrenia, epilepsy, amyotrophic lateral sclerosis, depression, multiple sclerosis, pain, schizophrenia, or have underlying excitotoxic mechanisms like depression, stroke and trauma, e.g. traumatic and/or spinal cord injury or other ischemic conditions in the brain. Generally, the compounds are applicable to all pathological conditions which have underlying excitotoxic and/or mitochondrial mechanisms.

The compounds of formula (I) may be used for prophylactic applications, e.g. to prevent or alleviate the outbreak of a disorder to be treated, and/or for therapeutic applications, e.g. to eradicate or alleviate an already manifest disorder.

For therapeutic and/or prophylactic applications, the compounds of formula (I) may be used alone or may be co-administered together with other medicaments, particularly neuroprotective medicaments and/or medicaments suitable for the prevention and/or treatment of neurologically-associated disorders. For example, the compounds of formula (I) may be co-administered together with neuroprotective peptides or proteins such as a neuregulin, particularly neuregulin isoforms as disclosed in PCT/EP 01/01424 and PCT/EP02/08778, which are herein incorporated by reference. Further, the compounds of formula (I) may be co-administered with Pirenzepine or other PARP-1 inhibitors, particularly with compounds as disclosed in PCT/EP2005/007804 and PCT/EP2005/007805, which are herein incorporated by reference, or with Mefloquine, Nelfinavir, Saquinavir and related protease inhibitors, particularly with compounds as disclosed in US 60/670,648, which is herein incorporated by reference.

A further aspect of the present invention relates to the use of a compound which is a modulator, e.g. an activator or inhibitor, of neuroprotective conditions via beta subunits of shaker-type voltage-gated potassium channels, particularly of nicotinic, e.g. a7-nicotinic, $GABA_A$ or NR2B-containing NMDA receptors, for the manufacture of a cytoprotective, particularly a neuroprotective medicament.

A further aspect of the present invention relates to the use of a compound which is a modulator, e.g. an activator or inhibitor, of neuroprotective conditions via members of solute carriers family 25, in particular aralar (member 12) and adenine-nucleotide translocator 1 & 2 (members 4 & 5) for the manufacture of a cytoprotective, particularly a neuroprotective medicament. Especially preferred is the use of a compound which is a modulator of Ant1.

A further aspect of the present invention relates to the use of a compound which is a modulator, e.g. an activator or inhibitor, of neuroprotective conditions via 4-nitrophenylphosphatase domain and non-neuronal SNAP25-like protein homolog 1 (NIPSNAP1) for the manufacture of a cytoprotective, particularly a neuroprotective medicament.

On the one hand, modulators may be selected from polypeptides capable of binding to the target protein, e.g. antibodies or antigen-binding fragments thereof. The antibodies may be selected from monoclonal antibodies, humanized antibodies, fully human antibodies or recombinant antibodies such as single-chain antibodies which are obtainable by standard methods in the art. Further examples of modulators are biologically active nucleic acids such as aptamers, i.e. nucleic acids capable of binding to the target molecule, antisense molecules, ribozymes or double-stranded RNA molecules capable of RNA interference. Further, the modulators may be small molecules, e.g. compounds of formula (I) or compounds which can be identified by an appropriate screening procedure which may comprise contacting a compound to be tested with a target molecule and determine inhibition and/or binding of the target molecule.

The compounds as indicated above are preferably administered to a subject in need thereof as a pharmaceutical composition, which may contain pharmaceutically acceptable carriers, diluents and/or adjuvants. The subject may preferably be a human being or an animal, particularly preferred a human being. The pharmaceutical composition may be administered in the form of a tablet, capsule, solution, suspension, aerosol, spray (e.g. nasal or throat spray), gel, plaster etc. The medicament may be administered according to any known means, wherein oral and intravenous administration is particularly preferred. The dose of the active ingredient depends on the type and the variety of disease and usually is in the range from 1 to 2000 mg/day, preferably in the range from 10 to 200 mg/day.

The present invention has applications in human and veterinary medicine, particularly in human medicine.

A further aspect of the present invention relates to the use of COAAA and/or AEOAA as a lead structure for the finding and/or development of a compound suitable for the above-mentioned use.

Furthermore, the present invention shall be illustrated by the following figures and examples.

BRIEF DESCRIPTION OF THE FIGURES

FIG. 1

FIG. 2

FIG. 3

FIG. 4

FIG. 5

FIG. 6

FIG. 7

FIG. 8

FIG. 9

EXAMPLES

1. Materials and Methods 1.1 Biological test system, Cell culture model for chemical ischemia, excitotoxic and β-amyloid-induced neuronal death and respective neuroprotection and for test of mitochondrial Permeability transition pore (MPTP)

For all experiments, D3 embryonic stem (ES) cells derived from 129/sv mice [Okabe et al., 1996] were cultivated for 12 days, with passages on days 2, 4, 7 and 9 as described previously [Sommer et al., 2004]. Insult conditions: Cells (24-well plates) were pre-incubated with or without 20 nM EPO (neuroprotective agent, positive control) in fresh medium for 24 hours at 37° C. Cells were rinsed once with low $K^+$ solution (140 mM NaCl, 4.7 mM KCl, 1.2 mM $KH_2PO_4$, 2.5 mM $CaCl_2$, 1.2 mM $MgSO_4$, 11 mM glucose, 15 mM Hepes-NaOH, pH 7.35). Cells (either with or without EPO pre-incubation) were incubated for up to 45 min (37° C.) with either low $K^+$ solution or with glucose-free low $K^+$ solution supplemented with 1 mM KCN chemical ischemia solution [Kume et al., 2002, Schrattenholz et al., 2005]. This insult relates to ischemic conditions in stroke. In addition similar cellular insults were established using glutamatergic agonists to induce excitotoxicity (Sommer et al., 2004) and respective neuroprotection related to stroke and epilepsy; and β-amyloid induced toxicity (incubation of neurons with 10 µM β-amyloid1-40 for 10 min, resulting in Ca-influx and neuronal death) and respective rescue related to Alzheimer's disease. Vitality control to assess numbers of surviving neurons was performed in all of these cases by a brief stimulation with a low dose of glutamate (10 µM). Afterwards, cells were washed three times with ice cold phosphate buffered saline (PBS), and then proteins were harvested. Suspended cells were pelleted at 500×G, and lysed into 9M urea 4% CHAPS. The cell lysate was desalted with a NAP-10 column (Amersham Biosciences), preequilibrated with the same buffer, and protein content was determined.

1.2 Calcium-Imaging

Functional tests by calcium imaging were performed essentially as described [Sommer et al., 2004]. Briefly, cells were loaded with 2 µM of fura-2 AM in DMEM for 45 min at 37° C. in the dark. Measurements of relative changes in

[Ca$^{2+}$] were made on an inverted epifluorescence microscope (Olympus IX70 S1F2) with a Polychrom IV Monochromator (Xe-lamp, USHIO). Excitation wavelengths ($\lambda_1$, $\lambda_2$) and the emission wavelength were 340, 380 and 510 nm, respectively. Acquisition and analysis of data after appropriate stimulation were performed by using MetaFluor software (Universal Imaging Corporation). Image resolution was 168×129 pixels (binning 8×8, pixel size 6.8×6.8 µm). Only cells identified as neurons by morphological criteria and occasional immunostaining (not shown) and those whose calcium levels returned to the resting state after the first stimulation were taken into account. Controls included nominal zero calcium (negative) and 5 µM ionomycin (positive), 10 µM glutamate (positive) and depolarisation (55 mM K+) (positive). Pharmacological agents were applied by a multi-valve, single-output focal drug application device (ALA Scientific) with the perfusion system DAD-12. Ratio images were displayed as a percentage of relative change in fluorescence over background fluorescence scale for comparison across experiments [as described in Sommer et al., 2004]. During each stimulation event 20 image pairs were acquired.

1.3. Functional Test of the MPTP by Rhodamine-123 Assay

Ant1 is one of the essential components of the MPTP, and thus was tested functionally by a fluorescent assay described by Metzger et al. (Metzger et al. Optical assessment of motoneuron function in a "twenty-four-hour" acute spinal cord slice model from fetal rats. Journal of Neuroscience Methods 141, 2005, 309320). Briefly, cells were incubated with Rhodamine-123 (10 g/ml) at 37° C. for 20 min. Rhodamine-123 was dissolved at 5 mg/ml in ethanol. For measurements of the membrane potential ψ, cells loaded with Rhodamine-123 were excited at 480 nm and emission was monitored at 565 nm. The lipophilic cation Rhodamine-123 accumulates in mitochondria where its fluorescence intensity is quenched at high concentrations (Chen, 1988; Scaduto and Grotyohann, 1999). A depolarizing change of ψ is indicated by an increase in the intensity of fluorescence in response to dequenching of the dye after release from mitochondria (Emaus et al., 1986; Duchen, 1992, 2000). Thus we refer to the relative change in ψ as the percentage change in Rhodamine-123 fluorescence (Schuchmann et al., 2000).

1.4. Chemical Proteomics; Synthesis of a Finasteride/Dutasteride Affinity Tag

Pregnenolone was used as a starting structure for the synthesis of an irreversible, i.e. covalently attached, Finasteride- or Dutasteride-related affinity reagent for target proteins. A reactive —SCN group binds to lysins in or near the binding site of the compound. A biotinylated linker serves for enrichment of bound protein. The synthesis is described in FIG. 1.

1.5. Identification and Characterization of Second Binding Site of Finasteride or Dutasteride The affinity tag was used to bind the target covalently from fractionations of crude cell extracts of D3 ES cells or rat brain membranes, subsequently the affinity purified material was analysed by 1D PAGE, immunostaining, and mass spectrometry. In the affinity tag incubation 0.5 NP 40-stem cell extract (2.3 mg protein) was incubated with 1 µM affinity tag for 60 min at 37° C. A surplus of affinity tag was removed by NAP10 gel filtration. The reaction mixture was bound to streptavidin agarose. After washing, elution of residually bound proteins occurred with elution buffer (2% SDS, 62.5 mM Tris-pH 6.8) for 10 min at room temperature and 10 min at 95° C.

1.6 Fractionation, Isolation, Mass Spectrometry

The subsequent fractionation, isolation and further analysis was performed according to published standard procedures (Sommer et al. 2004). Mass spectrometry for independent identification of Finasteride/Dutasteride-tagged proteins was performed as described elsewhere recently (Vogt et al., 2003, Cahill et al., 2003).

1.7 Autophagy-related Assays

Finasteride and Dutasteride have a marked effect in an assay for autophagy. Autophagy is the bulk degradation of proteins and organelles (Kim and Klionsky, 2000; Klionsky and Emr, 2000) and is significantly associated with cancer, infection, neurodegenerative diseases and cardiomyopathies (Mizushima et al., 2002; Klionsky, 2004; Tanida et al., 2004). Autophagy is also considered a particular non-apoptotic cell death pathway which has recently attracted considerable interest in the context of pathomechanisms underlying neurodegenerative diseases and neuroinflammatory or excitotoxic conditions in a variety of disease ranging from cancer to Alzheimer's disease (see e.g. Yorimitsu T, Klionsky D J. Autophagy: molecular machinery for self-eating. Cell Death Differ. 2005 November; 12 Suppl 2:1542-52; Tsujimoto Y, Shimizu S. Another way to die: autophagic programmed cell death. Cell Death Differ. 2005 November; 12 Suppl 2:1528-34; Levine B, Yuan J. Autophagy in cell death: an innocent convict? J Clin Invest. 2005 October; 115(10):2679-88). Moreover this type of non-apoptotic cell death appears to be related to mitochondria and the MPTP (Kim R, Emi M, Tanabe K. Role of mitochondria as the gardens of cell death Cancer Chemother Pharmacol. 2005 Sep. 21; 1-9 [Epub ahead of print]; Bota D A, Davies K J. Protein degradation in mitochondria: implications for oxidative stress, aging and disease: a novel etiological classification of mitochondrial proteolytic disorders. Mitochondrion. 2001 June; 1(1):33-49)

Essentially we followed the procedure described in Proikas-Cezanne et al. (Proikas-Cezanne T. Waddell S, Gaugel A, Frickey T, Lupas A, Nordheim A. WIPI-1alpha (WIPI49), a member of the novel 7-bladed WIPI protein family, is aberrantly expressed in human cancer and is linked to starvation-induced autophagy. Oncogene. 2004 Dec. 16; 23(58):9314-25). The presence of autophagy is quantified by a polyclonal hWIPI-1 antiserum, which was generated by immunizing rabbits (Charles River) with two synthetic peptides representing C-terminal regions in hWIPI-1 (363nkendlrpslp373, 407lrgevipehefatgpv422) and used at a dilution of 1:5000 in ECLWestern blotting detections (Amersham), and at 1:250 for indirect immunofluorescent stainings.

For these stainings, cells were fixed in 3.7% paraformaldehyde (15 min, RT) and analysed by confocal microscopy (see below). To visualize endogenous hWIPI-1 in G361 cells consecutive incubations were conducted using C-terminal hWIPI-1 antiserum at 1:250 (30 min, RT) and Alexa 546 or Alexa 488 labelled goat anti-rabbit IgG (Molecular Probes) at 1:500 (30 min, RT) in PBS/0.1% Tween (blocking/permeabilization: PBS/0.1% Tween/1% BSA, 30 min RT; washing: PBS/0.1% Tween). For nuclear staining, TO-PRO-3 (Molecular Probes) was used at 1:1000. Finally, cells were mounted in Vectashield Mounting Medium (Vector Laboratories) and kept in the dark (41C). Confocal laser scanning microscopy was conducted using a LSM510 microscope (Zeiss) and a 63_ 1.4 DIC Plan-Apochromat oil-immersion objective. GFP and Alexa 488 were excited at 488 nm with the internal argon-ion laser. Alexa 546 and TO-PRO-3, respectively, were excited at 543 and 633 nm with helium-neon lasers. A series of 10-20 sections with 0.5 mm spacing along the z-axis was taken and projections were created from confocal stacks by merging the individual confocal slices 1.8 Electrophysiology Xenopus oocytes were transfected with various subunit combinations of potassium channels, like Kv1.5+Kvβ2.1. Subsequently activation curves using inside-out patches (external: 2 mM K+, internal: 96 mM K+) were measured, they represent IV-curves using standard internal buffer solution (HK+), which were recorded in the presence and absence of 1 µM Finasteride. Corresponding plots of G/Gmax versus the membrane potential were used to evaluate related effects.

Figure 9:
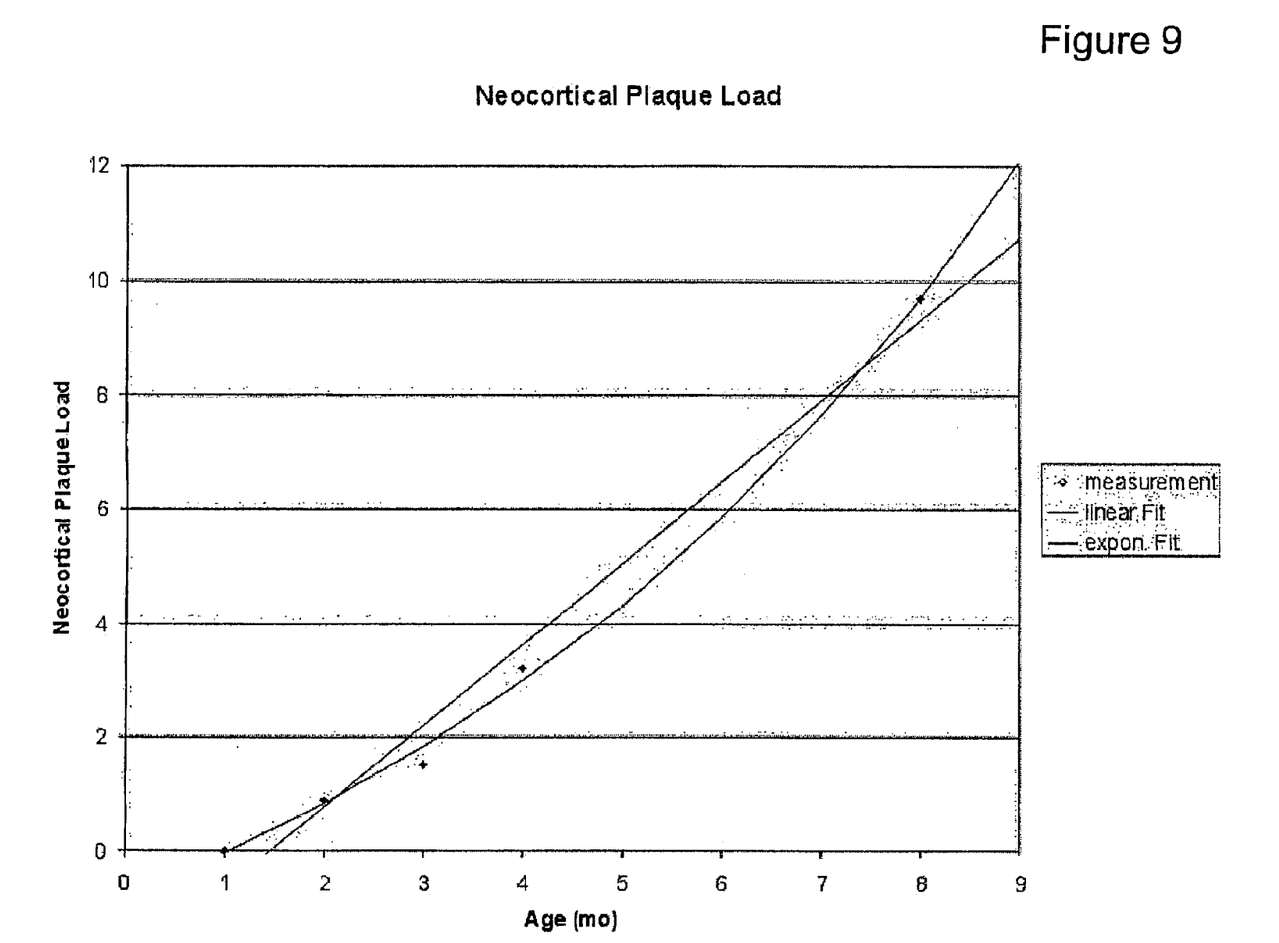
FIG. 9 shows a reduction of neocortical plaque load in Dutasteride-treated animals compared to non-treated controls.

1.9 In vivo Assay for Determining the Effect of Dutasteride on the Formation of β-Amyloid Plaques in a Mouse Model of Alzheimer's Disease A quite aggressive model for Alzheimer's disease is a double transgenic mouse line expressing mutated human amyloid precursor protein (APP) and presinilin-1 (PS). Between months 4 and 5 a maximal additional increase of the plaque load of 35-40% can be expected (exponential fit, FIG. 9).

Dutasteride was administered orally every day after animals became 4 months old, for 30 days at a maximum concentration of 2 mg/day.

Technically, images were recorded from whole brain sections (Olympus Fluorescence microscope AX70, Digital camera Casio QV4000; resolution 2240×1680 Pixel, with constant overall intensity in all images) A software-assisted procedure was then used to quantify overall areas of NT12 stain (anti-β-amyloid stain) (plaque area), and NT12 stain volumes in these areas by defining thresholds and relating them to overall proportions of respective slices (plaque volume).

Figure 2:
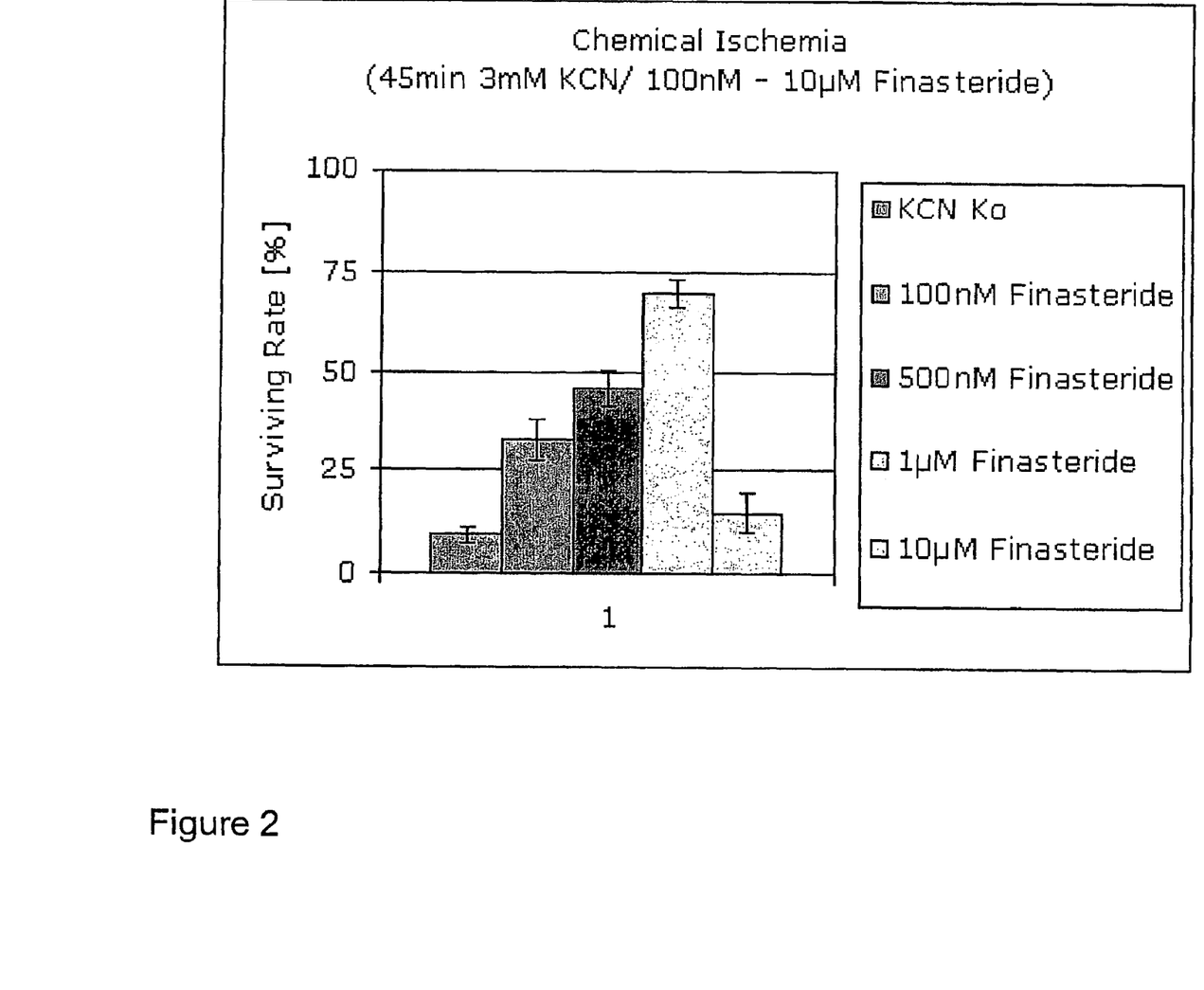
FIG. 2 shows neuroprotection against neuronal death induced by chemical ischemia, a condition which without administration of Finasteride at concentrations indicated results in death of most of cultured neurons (green bar). The presence of 100 nM-1 µM Finasteride during the ischemic insult results in substantial protection. Surviving rate of neurons is quantified by counting distinct functionally active neurons before and after insult.

2. Results 2.1. Neuroprotective Effect of Finasteride and Dutasteride in Chemical Ischemia FIG. 2 shows a dose response relationship of the neuroprotective effect of Finasteride in the functional model outlined in the methods section. The effect peaks at about 1 µM. At higher concentrations the effect is decreasing again.

Whereas control cells had a surviving rate 4.8±3.4% (number of cells at first stimulation: 189 and number of cells at second stimulation after chemical ischemia: 9), Finasteride-treated (1 µM) cells had a surviving rate of 72.1±4.4% (number of cells at first stimulation: 136 and number of cells at second stimulation after chemical ischemia: 98). Similar experiments were performed using an excitotoxic paradigm with glutamatergic agonists (100 µM NMDA, like in Sommer et al., 2004) and by rescue against β-amyloid-induced neuronal death (10 µM Aβ1-40). All three conditions induce an initial rise in intracellular calcium which is accompanied by a characteristic set of changes on the level of fast posttranslational modifications, like phosphorylation and methylation of a signature of stress-related proteins (Sommer et al., 2004; Schrattenholz et al., 2004). This protein biomarker signature allows a molecular control of neurotoxic/neuroprotective events during the course of these experiments, and moreover relates to respective mode of actions of neuroprotective agents.

Figure 3:
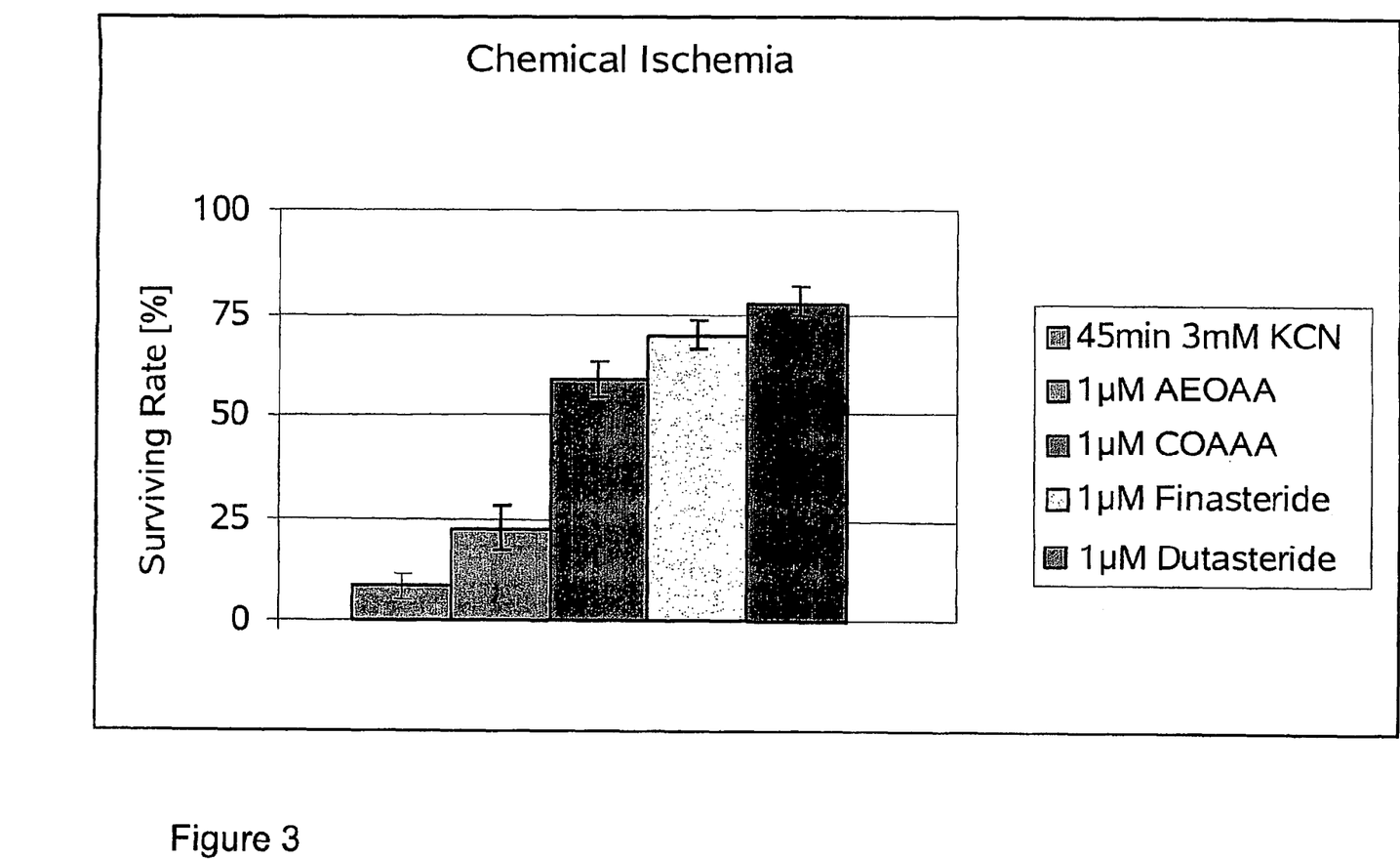
FIG. 3 shows neuroprotective effects of derivatives of Finasteride, Dutasteride and related compounds. Surviving rate of neurons is quantified by counting distinct functionally active neurons before and after insult, in this experiment n=200 for each column.

FIG. 3 shows corresponding experiments with two derivatives of Finasteride and Dutasteride, AEOAA: 4α,6α-Dimethyl-2-oxo-hexadecahydro-indeno[5,4-f]quinoline-7-carboxylic-(2-amino-ethyl)-amide hydrochloride COMA: 4α,6α-Dimethyl-2-oxo-hexadecahydro-indeno[5,4-f]quinoline-7-carboxylic acid; at each 1 µM, the neuroprotective effect of Finasteride and Dutasteride is comparable and strongest, with COMA being nearly as efficacious, whereas AEOAA is considerably less active.

Similar experiments were performed using 10 µM β-amyloid1-40 as neurotoxic agent and 100 µM NMDA in an excitotoxic paradigm. The EC50 values of the corresponding neuroprotective effects of Finasteride/Dutasteride and some derivatives are given in Table 1:

TABLE 1

EC50 values (in µM) of neuroprotective effects of Finasteride, Dutasteride and derivatives observed in the in vitro model outlined in the methods section.

|  | Excitotoxic paradigm (100 µM NMDA) (µM) | β-amyloid toxicity (10 µM Aβ 1-40) (µM) | Chemical ischemia (µM) |
| --- | --- | --- | --- |
| Finasteride | 2 | 0.1 | 0.3 |
| Dutasteride | 1.5 | 0.1 | 0.3 |
| AEOAA | 5 | 4 | 5 |
| COAAA | 5 | 2 | 1 |

AEOAA: 4α,6α-Dimethyl-2-oxo-hexadecahydro-indeno[5,4-f]quinoline-7-carboxylic-(2-amino-ethyl)-amide hydrochloride COAAA: 4α,6α-Dimethyl-2-oxo-hexadecahydro-indeno[5,4-f]quinoline-7-carboxylic acid.

2.2 Identification of Targets of Finasteride/Dutasteride

Figure 4:
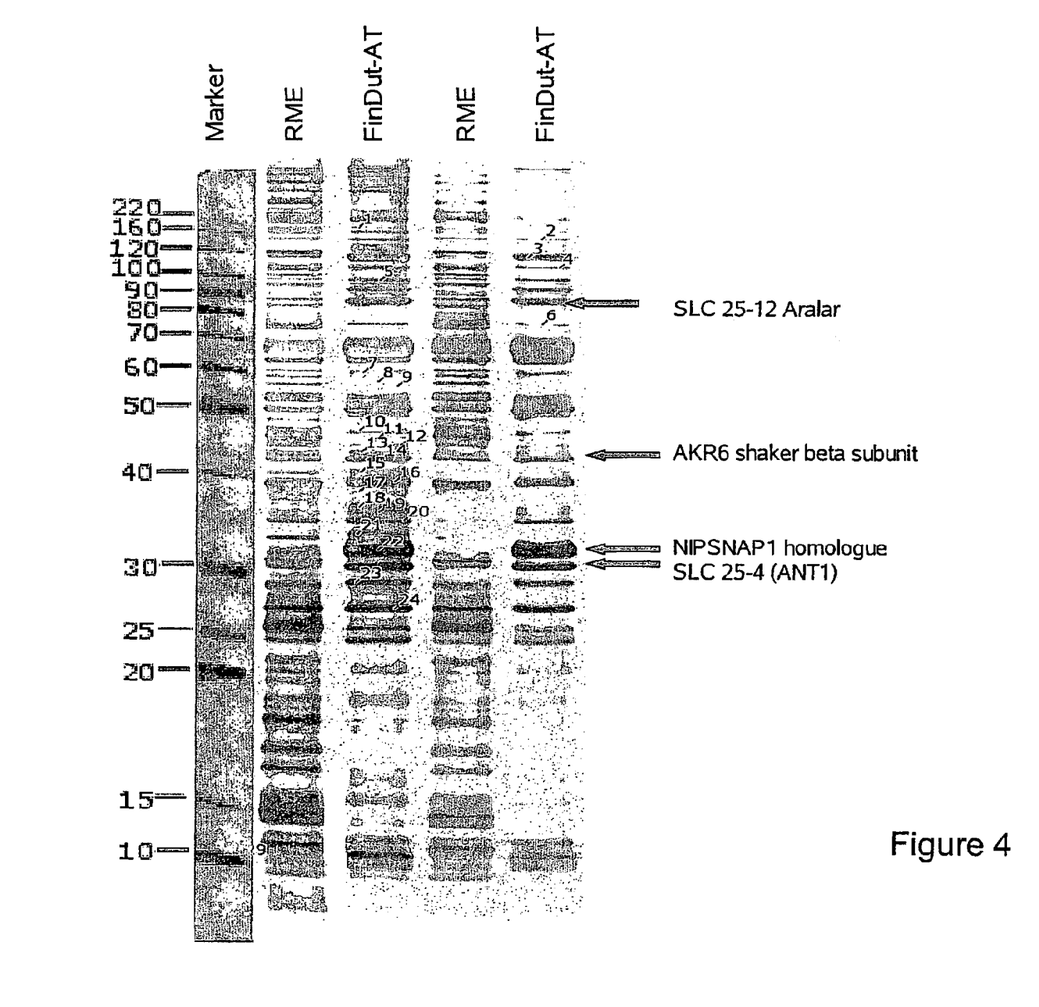
FIG. 4 shows enrichment of proteins which react with Finasteride and Dutasteride-affinity tag (FinDut-AT) under conditions described. Raw membrane extract (RME) and the enriched fraction FinDut-AT have been analysed at two different concentrations (5 and 2.5 µg of protein per lane, respectively) on silver stained 1D gels. Only those proteins which were specifically associated with Finasteride and Dutasteride are indicated by arrows. Table 2 gives the details of the identification of enriched proteins by mass spectrometry.

FIG. 4 shows that the Finasteride/Dutasteride-affinity tag prepared according to the Methods section selectively enriches certain proteins from neuronal cell culture or rat brain preparations as demonstrated by silver staining appropriate 1D gels of extracts of V56 cells. Only those bands marked with arrows contained proteins enriched as compared to the raw extract profiles. All other bands were either present in both lanes (raw membrane extract, RME and Finasteride/Dutasteride-affinity tag, FinDut-AT). In the case of the AKR6 shaker potassium channel beta subunit 2 (Kv-beta-2), a corresponding band at approx. 40 kD in the RME only contained glycerolaldehyde-dehydrogenase, a housekeeping protein, absent in the FinDut-AT enriched fractions, some additional bands seemingly enriched are similarly from mainly structural proteins (details not shown), potentially loosely associated with Kv-beta-2; details of those 5 proteins claimed to be Finasteride/Dutasteride-specific new targets, are provided in table 2. Since the affinity tag reacted covalently via a SCN-group (FIG. 1), competition with a huge excess of Finasteride or Dutasteride (10 mM) was only achieved to a very limited extent, when applied during the first minute of incubation (data not shown), nevertheless indicating a specific reaction.

TABLE 2

Mass spectrometry-based identification of Finasteride/Dutasteride-affinity tag-enriched proteins; PMF (peptide mass fingerprint) score: Mowse score, identification is considered significant if score is bigger than 60; experimental molecular weight are given, as well as calculated isoelectric points (pI) and molecular weights; AccNo are the gene bank accession numbers for the proteins identified.

| exp. | | PMF | | theor. | | |
| --- | --- | --- | --- | --- | --- | --- |
| PI | MW | Score | AccNo | pI | MW | Description |
|  | 45000 | 84 | gi\|31543030 | 9.4 | 40995 | Potassium voltage-gated channel, shaker-related subfamily, beta member 2; potassium voltage gated channel, shaker related |

TABLE 2-continued

Mass spectrometry-based identification of Finasteride/Dutasteride-affinity tag-enriched proteins; PMF (peptide mass fingerprint) score: Mowse score, identification is considered significant if score is bigger than 60; experimental molecular weight are given, as well as calculated isoelectric points (pI) and molecular weights; AccNo are the gene bank accession numbers for the proteins identified.

| exp. | | PMF | | theor. | | |
|---|---|---|---|---|---|---|
| PI | MW | Score | AccNo | pI | MW | Description |
| | | | | | | subfamily, beta member 2 [*Mus musculus*] |
| | | 83 | gi\|975314 | 9.5 | 41154 | Potassium channel beta 2 subunit |
| | | 70 | gi\|18202524 | 9.4 | 40959 | Voltage-gated potassium channel beta-2 subunit (K+ channel beta-2 subunit) (Kv-beta-2) |
| | 28000 | 120 | gi\|32189350 | 10.3 | 32880 | Solute carrier family 25, member 5; adenine nucleotide translocator 2, fibroblast isoform (ATP-ADP carrier protein); Adenine nucleotid translocator 2 fibroblast isoform (ATP-ADP carrier protein) [*Rattus norvegicus*] |
| | 76000 | 241 | gi\|27369581 | 8.5 | 74523 | Solute carrier family 25 (mitochondrial carrier, Aralar), member 12 [*Mus musculus*] |
| | 33000 | 121 | gi\|52000650 | 8.5 | 32927 | ADP, ATP carrier protein 1 (ADP/ATP translocase 1) (Adenine nucleotide translocator 1 ) (ANT 1) (Solute carrier family 25, member 4) (CSQ-binding 30 kDa protein) |
| | | 155 | gi\|13124050 | 8.6 | 74709 | Calcium-binding mitochondrial carrier protein Aralar1 (Mitochondrial aspartate glutamate carrier 1) (Solute carrier family 25, member 12) |
| | 33000 | 121 | gi\|34879019 | 9.8 | 33325 | Similar to NIPSNAP1 protein [*Rattus norvegicus*] |
| | | 121 | gi\|6679066 | 9.9 | 33342 | 4-nitrophenylphosphatase domain and non-neuronal SNAP25-like protein homolog 1 [*Mus musculus*] |

2.3 K+ Channel Electrophysiology

Figure 5:
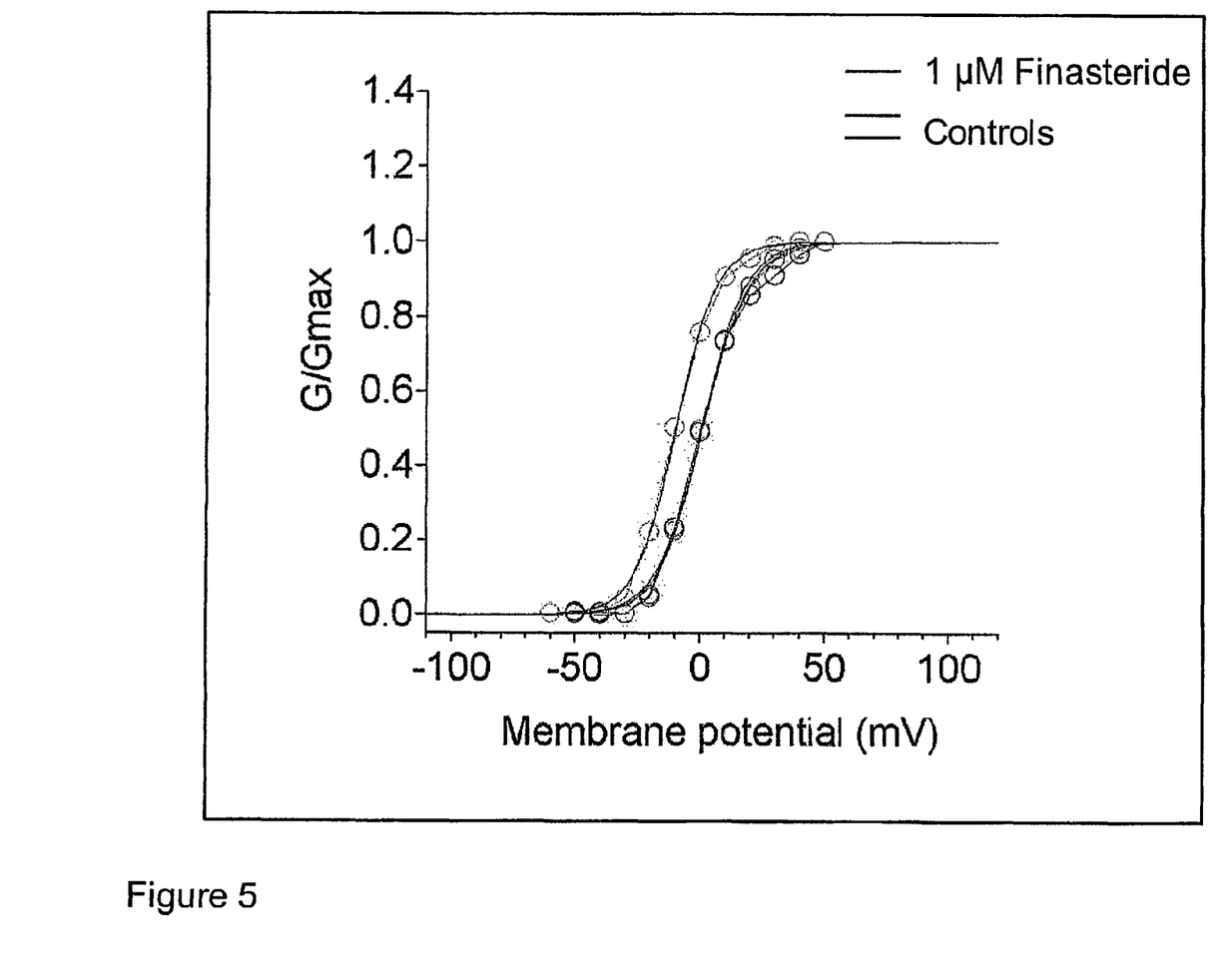
FIG. 5 shows that Finasteride modulates the channel properties of various voltage-gated potassium channels via the beta subunits.

As shown in FIG. 5, Finasteride modulates the channel properties of various voltage-gated potassium channels via the beta subunits. The effect is subtle but visible, Xenopus oocytes transfected with Kv1.5 and Kvβ2.1 show in inside-out patches a small shift of the IV-curve towards more negative potential in corresponding plots of G/Gmax versus the membrane potential in the presence of e.g. 1 μM Finasteride. Similar effects were seen for other potassium channel subunit combinations and for Dutasteride and COMA (not shown).

2.4 MPTP Assay with Rhodamine-123

Figure 6:
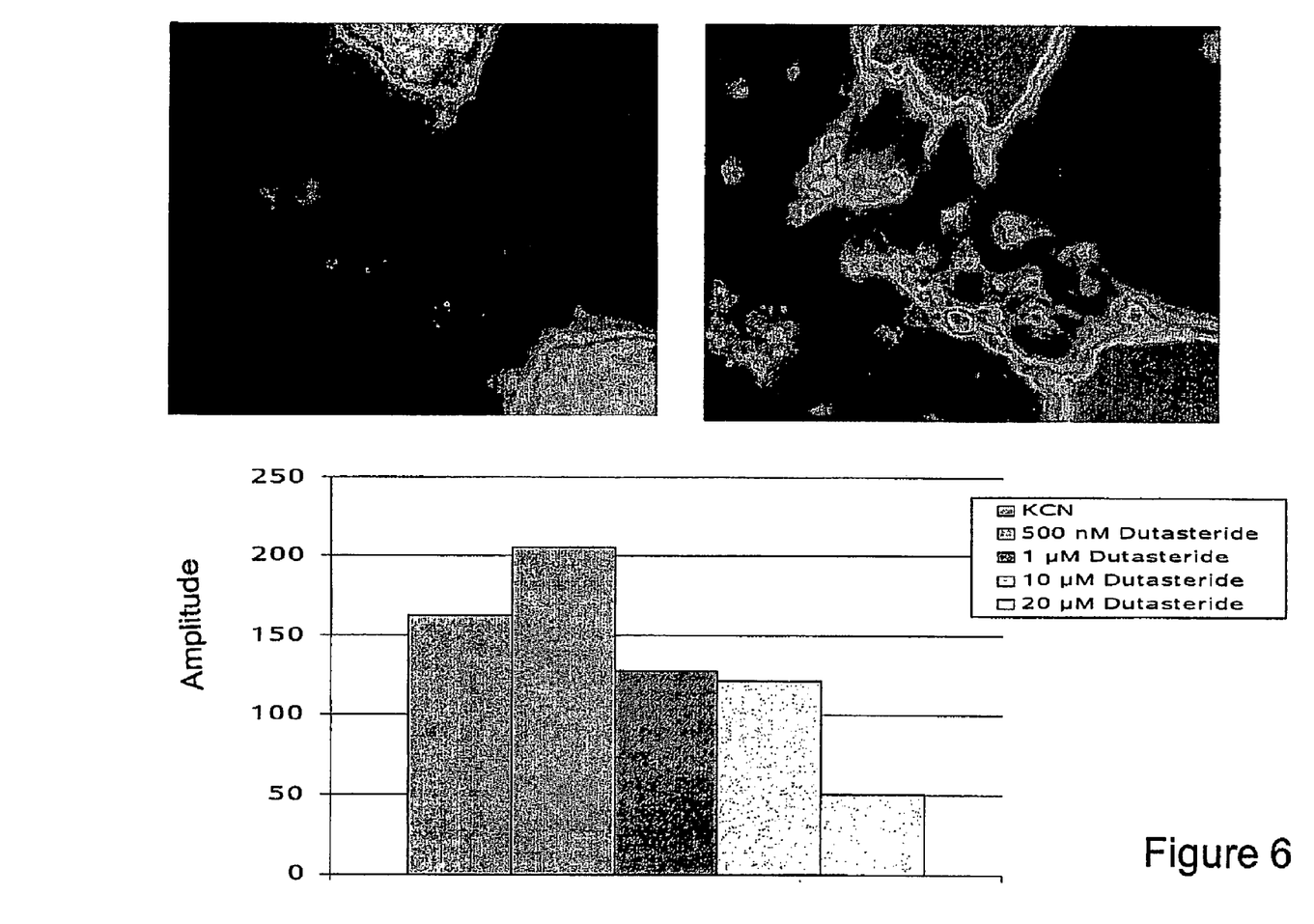
FIG. 6 shows a dose-dependent effect of Dutasteride by inhibiting release of the fluorescent dye Rhodamine-123 from mitochondria in a mitochondrial permeability transition pore (MPTP) assay.

As shown in FIG. 6, Dutasteride (and Finasteride, not shown), have both a similar dose-dependent (0.5, 1, 10, 20 μM) effect by inhibiting release of the fluorescent dye Rhodamine-123 from mitochondria after initiation and opening of the MPTP. In the upper part to images are shown, before (left) and after (right) induction of ischemic conditions in neural derivatives of embryonic stem cells (Sommer et al., 2004, Schrattenholz et al., 2005), which next to massive calcium transients, induce a rapid opening of the MPTP, measured by de-quenching of Rhodamine-123 released to the cytosol. Dutasteride causes a marked and significant inhibition of MPTP-formation and opening during ischemic conditions, probably by binding to Ant1 and thus confers neuroprotection to challenged cells.

2.5 Autophagy-related Assay Employing WIPI-staining

Figure 7:
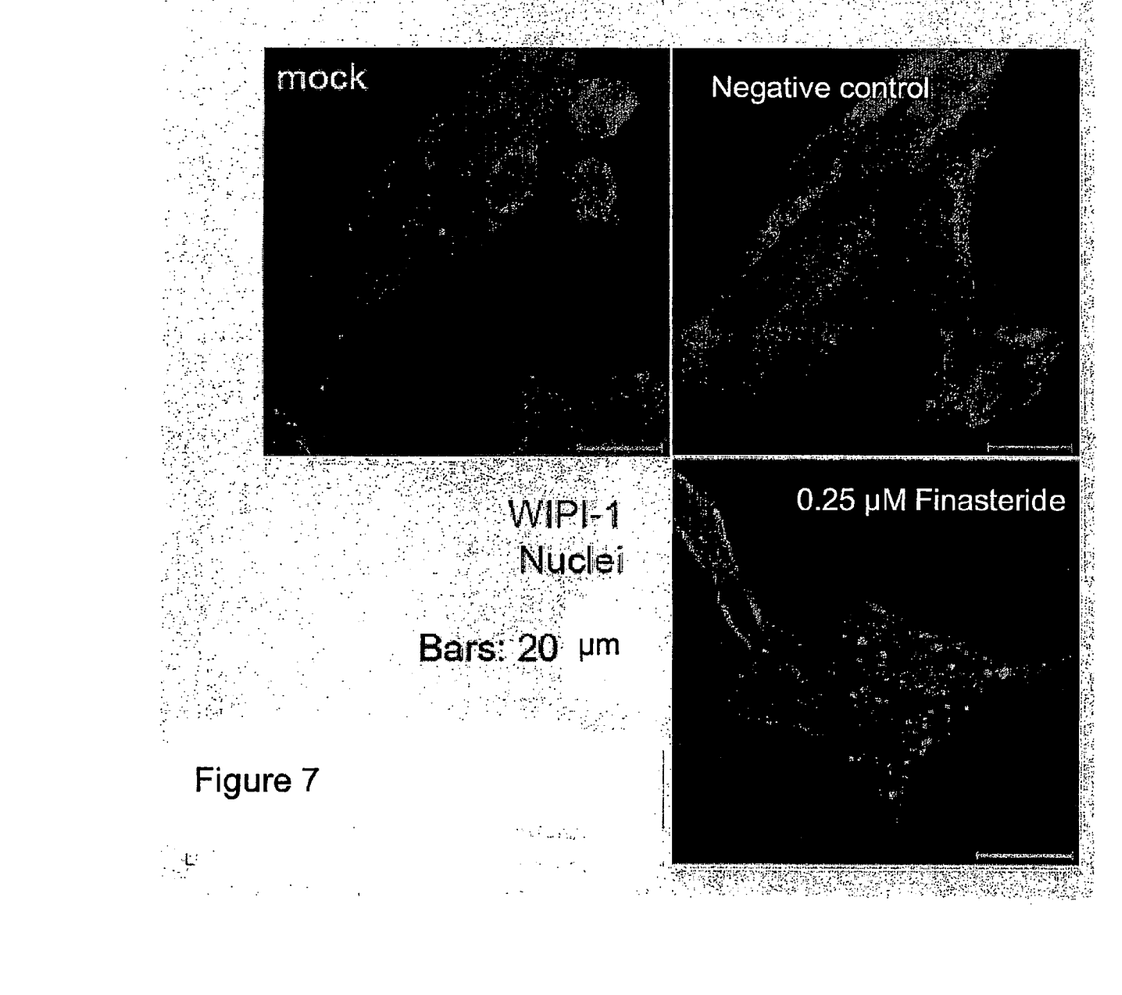
FIG. 7 shows a dose-dependent effect of Finasteride on the enhancement of autophagy in G361 cells.

As shown in FIG. 7, Finasteride (and Dutasteride, not shown) have a dose-dependent effect (0.25, 0.5, 1.0 or 2.0 μM were tested) on the enhancement of autophagy in surviving G361 cells, in a functional assay for the identification of modulators of human autophagy by indirect immunoflourescence of endogenous WIPI-1 and co-staining of lysosomes and nuclei followed by confocal microscopy (for details see Proikas-Cezanne et al., 2004).

2.6 Results of In Vivo Experiments in a Mouse Model for Alzheimer's Disease (APPPS Mice)

Figure 8:
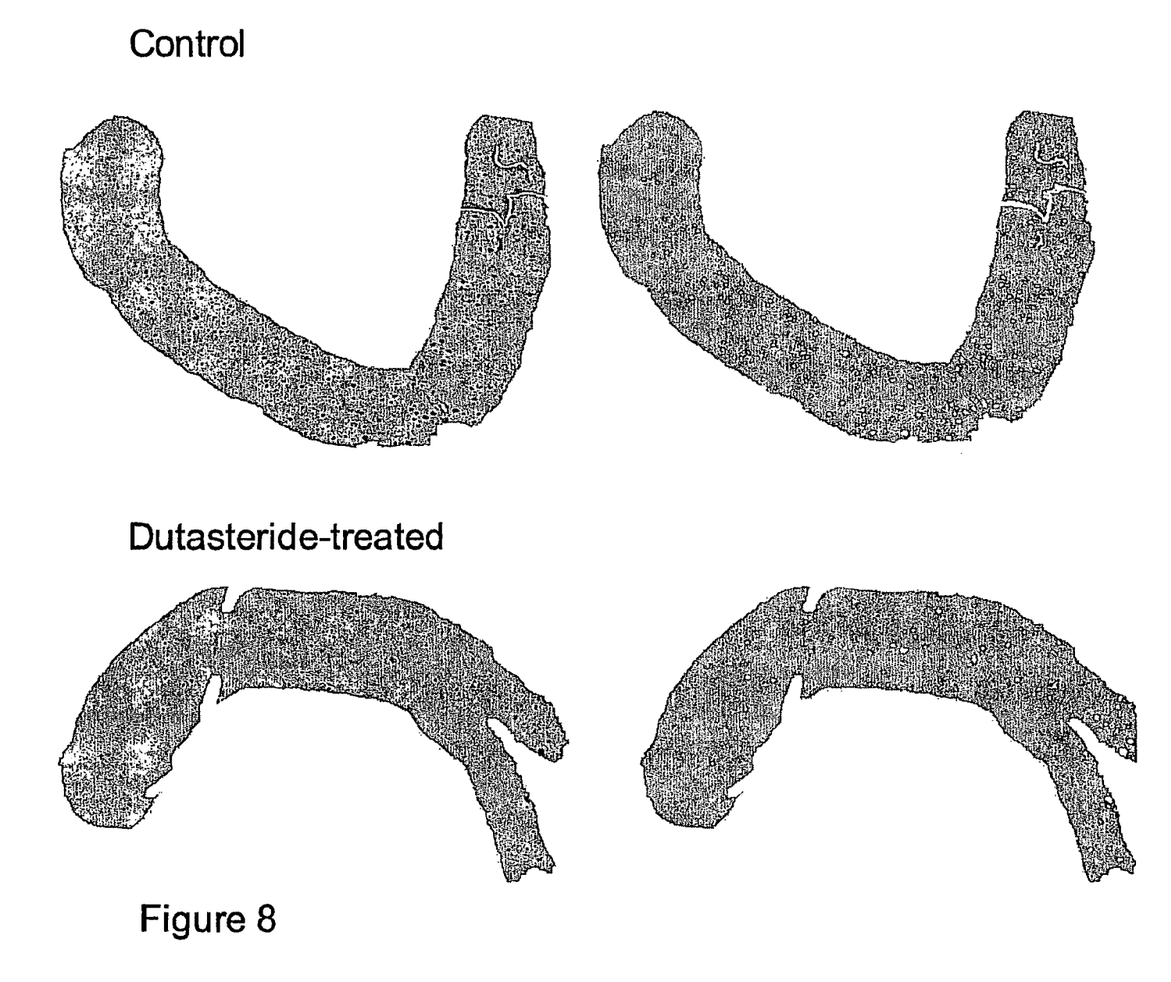
FIG. 8 shows a comparison of cortical slices from a Dutasteride-treated and a non-treated control animal stained with NT-12 antibody directed against β-amyloid plaques.

As shown in FIG. 8 with two representative examples of cortical slices from each a Dutasteride-treated and a non-treated control animal, the load of β-amyloid plaques (stained with NT12 antibody) is significantly lower in the treated group. A computer-assisted quantification of several hundred slices from each eight transgenic animals (APPPS mice) for treated and non-treated groups Briefly, as can be seen from the graph in FIG. 9, which was derived from the NT12 staining of cortical slices (see manuscript) it is evident that in this quite aggressive model between months 4 and 5 a maximal additional increase of the plaque load of 3540% can be expected (exponential fit). This was the window of the experiments performed Dutasteride, where we observed overall reductions of 12 and 13%, respectively) as compared to non-treated controls.

For the amplitude of expected signal between months 4 and 5, this translates to at least 30-32.5% reduction of the plaque load which is an unexpectedly clear effect. These results are statistically significant with β-values of 0.001-0.0005, depending on whether we quantify plaque area or plaque volume (see Methods section)

There is a high correlation of the NT12 stain for β-amyloid and a corresponding microglial stain (correlation coefficient r=0.60), (not shown).

2.7 Conclusions

Our results clearly show that Finasteride, Dutasteride and related compounds can exert neuroprotective effects in different experimental paradigms, related to human neurodegenerative diseases and conditions, like epilepsy, Morbus Alzheimer, Morbus Parkinson and others, via a novel mechanism which involves voltage-gated potassium channel beta subunits ($K_v$beta) and several members of SLC family, (in particular Ant1 of the MPTP) as, previously unknown targets of the compound. The direct effects on functional potassium channels are relatively small, but measurable. We have indications, that the AKR6-function of $K_v$beta is important in modulating other ionotropic ligand-gated channels, like $GABA_A$-, α7-nicotinic and NMDA receptors, from the latter in particular those with NR2B subunits (which are supposed to be regulated by steroids). In the brain this target may play an important role, whereas the original target, 5-α-dehydrogenase plays a minor role in the brain.

A clear effect can however be quantified on the level of the MPTP by a fluorescent assay employing Rhodamine-123, the most important major factor in the induction of the so-called intrinsic apoptotic (mitochondrial) pathway. Finasteride and Dutasteride clearly inhibit in a dose-dependent manner the opening of the mitochondrial pore, moreover in a concentration range which corresponds to the respective range of neuroprotective effects in in vitro and in vivo assays (FIGS. 2 & 3, 8). Without wishing to be bound by theory, we conclude that the binding of Finasteride and Dutasteride to various members of the solute carrier family 25 (SLC 25) is responsible for this effect, in particular binding to Ant1, an essential constituent of the MPTP is assumed to underlying the neuroprotective effects and the inhibition of MPTP opening, and thus induction of intrinsic mitochondrial apoptotic pathways.

This property of Finasteride, Dutasteride and related compounds was previously unknown and allows the conclusion that Finasteride/Dutasteride/Dutasteride and related compounds may be used as cytoprotective, e.g. neuroprotective agents for medical applications.

The neuroprotective properties of Finasteride, Dutasteride and related compounds are rather due to this hitherto unknown multiple mode of action, which became apparent by a focussed drug repositioning program.

REFERENCES

1. Cahill M A, Wozny W, Schwall G, Schroer K, Holzer K, Poznanovic S, Hunzinger C, Vogt J A, Stegmann W, Matthies H, Schrattenholz A. (2003). Analysis of relative isotopologue abundances for quantitative profiling of complex protein mixtures labelled with the acrylamide/D3-acrylamide alkylation tag system. Rapid Communications in Mass Spectrometry, 2003, 17:1283-1290
2. Sommer S, Hunzinger C, Schillo S, Klemm M, Biefang-Arndt K, Schwall G, Pütter S, Hoelzer K, Schroer K, Stegmann W Schrattenholz A (2004) Molecular analysis of homocysteic acid-induced neuronal stress. Journal of Proteome Research 3, in press
3. Okabe S, Forsberg-Nilsson K, Spiro A C, Segal M, McKay R D G. Development of neuronal precursor cells and functional postmitotic neurons from embryonic stem cells in vitro. Mech Dev. 59: 89-102, 1996
4. Kume T, Nishikawa H, Taguchi R, Hashino A, Katsuki H, Kaneko S, Minami M, Satoh M, Akaike A. Antagonism of NMDA receptors by sigma receptor ligands attenuates chemical ischemia-induced neuronal death in vitro. Eur J. Pharmacol. 455:91-100, 2002
5. Shevchenko A, Wilm M, Vorm O, Mann M. (1996). Mass spectrometric sequencing of proteins silver-stained polyacrylamide gels. Analytical Chemistry. 1996; 68:850-858
6. Vogt J A, Schroer K, Holzer K, Hunzinger C, Klemm M, Biefang-Arndt K, Schillo S, Cahill M A, Schrattenholz A, Matthies H, Stegmann W. (2003). Protein abundance quantification in embryonic stem cells using incomplete metabolic labelling with 15N amino acids, matrix-assisted laser desorption/ionisation time-of-flight mass spectrometry, and analysis of relative isotopologue abundances of peptides. Rapid Commun Mass Spectrom. 2003; 17:1273-1282
7. Vuong G L, Weiss S M, Kammer W, Priemer M, Vingron M, Nordheim A, Cahill M A, (2000) Improved sensitivity proteomics by post harvest alkylation and radioactive labelling of proteins. Electrophoresis, 2000; 21:2594-2605
8. Schrattenholz, A. et al. (2005) Differential and quantitative molecular analysis of ischemia complexity reduction by isotopic labeling of proteins using a neural embryonic stem cell model. J. Neurol. Sci. 229-230, 261-267
9. Chen L B. Mitochondrial membrane potential in living cells. Annu Rev Cell Biol 1988; 4:155-81
10. Scaduto Jr R C, Grotyohann L W. Measurement of mitochondrial membrane potential using fluorescent rhodamine derivatives. Biophys J 1999; 76:469-77.
11. Emaus R K, Grunwald R, Lemasters J J. Rhodamine 123 as a probe of transmembrane potential in isolated rat-liver mitochondria: spectral and metabolic properties. Biochim Biophys Acta 1986; 850:436-48.
12. Duchen M R. Ca(2+)-dependent changes in the mitochondrial energetics in single dissociated mouse sensory neurons. Biochem J 1992; 283(Pt 1):41-50.
13. Duchen M R. Mitochondria and calcium: from cell signalling to cell death. Physiol 2000; 529(Pt 1):57-68.
14. Schuchmann S, Luckermann M, Kulik A, Heinemann U, Ballanyi K. Ca (2+)- and metabolism-related changes of mitochondrial potential in voltage-clamped CA1 pyramidal neurons in situ. J Neurophysiol 2000; 83:1710-21.
15. Kim J, Klionsky D J. Autophagy, cytoplasm-to-vacuole targeting pathway, and pexophagy in yeast and mammalian cells. Annu Rev Biochem. 2000; 69:303-42.
16. Klionsky D J, Emr S D. Autophagy as a regulated pathway of cellular degradation. Science. 2000 Dec. 1; 290(5497): 1717-21.
17. Mizushima N, Ohsumi Y, Yoshimori T. Autophagosome formation in mammalian cells. Cell Struct Funct. 2002 December; 27(6):421-9.
18. Klionsky D J Cell biology: regulated self-cannibalism. Nature. 2004 Sep. 2; 431 (7004):31-2.
19. Tanida I, Ueno T, Kominami E. LC3 conjugation system in mammalian autophagy. Int J Biochem Cell Biol. 2004 December; 36(12):2503-18.
20. Schrattenholz A (2004) Proteomics: How to control highly dynamic patterns of millions of molecules and interpret changes correctly? Drug Discovery Today-Technologies 1, 1-8
21. Proikas-Cezanne T, Waddell S, Gaugel A, Frickey T, Lupas A, Nordheim A. WIPI-1alpha (WIPI49), a member of the novel 7-bladed WIPI protein family, is aberrantly expressed in human cancer and is linked to starvation-induced autophagy. Oncogene. 2004 Dec. 16; 23(58):9314-25

The invention claimed is:

1. A method for the treatment of neurologically-associated disorders in a subject in need of such treatment, wherein said neurologically-associated disorder is Parkinson's disease, which comprises administering to said subject a therapeutically effective amount of a compound of formula (I)

wherein

R1 and R2 are independently of one another in each case hydrogen or methyl,

R3 is hydroxy,
$C_1$-$C_8$-alkyl, $C_3$-$C_8$-cycloalkyl $C_1$-$C_8$-alkoxy $C_1$-$C_8$-monoor dialkylamino or $C_1$-$C_8$-alkyldiamino wherein each of the preceding residues can be unsubstituted or substituted by one to three substituents, independently of one another selected from the group consisting of hydroxy, halo, cyano, $C_1$-$C_4$-alkyl, $C_1$-$C_4$-alkoxy and phenyl, heteroaryl, heteroaryloxy, heteroarylamino, aryl, aryloxy or arylamino, wherein the heteroaryl or aryl moiety of each of the preceding residues can be unsubstituted or substituted by one to three substituents, independently of one another selected from the group consisting of hydroxy, halo, cyano $C_1$-$C_4$-alkyl, C1-C4-alkoxy trihalomethyl phenyl and phenyloxy, $R^4$, $R^5$ and $R^6$ are independently of one another in each case hydrogen or $C_1$-$C_8$ alkyl n is 0 or 1 and ------ is a double or a single bond, or of a salt thereof.

2. A method according to claim 1, which comprises administering to said subject an amount in the range from 1 to 2000 mg of the compound of formula (I) per day.

3. A method according to claim 1, which method comprises the interaction between the compound of formula (I) and the protein AKR6.

4. A method according to claim 1, which method comprises the interaction between the compound of formula (I) and a protein selected from Aralar1 (SLC 25-12), adenine nucleotide translocator 1 (SLC 25-5) and NIPSNAP1.

5. A method according to claim 1, which method comprises administering to the subject a pharmaceutical composition comprising a compound of formula (I) and a pharmaceutically acceptable carrier, diluent and/or adjuvant, the pharmaceutical composition being in the form of a tablet, capsule, solution, suspension, nasal spray, throat spray, gel or plaster.

6. The method of claim 1, wherein in the compound of formula (I) independently of each other $R^1$ is hydrogen or methyl, $R^2$ is methyl, $R^3$ is hydroxy, $C_1$-$C_8$-mono- or dialkylamino, $C_1$-$C_8$-alkyldiamino or arylamino, wherein the aryl moiety is substituted by one to three substituents, independently of one another selected from the group consisting of hydroxy, halo, cyano, $C_1$-$C_4$-alkyl, $C_1$-$C_4$-alkoxy or trihalomethyl, $R^4$ is hydrogen, a-methyl or 13-methyl, $R^5$ is hydrogen or 13-methyl, $R^6$ is hydrogen, methyl or ethyl, n is 0, and/or ------ is a double or single bond.

7. The method according to claim 1, in which the compound of formula (I) is a compound selected from 17β-(N-tert-butylcarbamoyl)-4-aza-5a-androst-1-en-3-one, 17β-(N-isobutylcarbamoyl)-4-aza-5a-androst-1-en-3-one, 17β-(N-tert-octylcarbamoyl)-4-aza-5a-androst-1-en-3-one, 17β-(N-octylcarbamoyl)-4-aza-5a-androst-1-en-3-one, 17β-(N-1,1-diethylbutylcarbamoyl)-4-aza-5a-androst-1-en-3-one, 17β-(N-neopentylcarbamoyl)-4-aza-5a-androst-1-en-3-one,

17β-(N-tert-amylcarbamoyl-4-aza-5a-androst-1-en-3-one, and

17β-(N-tert-hexylcarbamoyl)-4-aza-5a-androst-1-en-3-one.

8. The method according to claim 1, in which the compound of formula (I) is 17β-(N-tert-butylcarbamoyl)-4-aza-5a-androst-1-en-3-one.

9. A method for the treatment of neurologically-associated disorders in a subject in need of such treatment, wherein said neurologically-associated disorder is Parkinson's disease, which comprises administering to said subject a therapeutically effective amount of 5α, 17β-N-[2,5-bis(trifluoromethyl)phenyl]-3-oxo-4-azaandrost-1-ene-17-carboxamide.

10. The method according to claim 1, in which the compound of formula (I) is

COAAA

4α,6α-dimethyl-2-oxo-hexadecahydro-indeno[5,4-f]quinoline-7-carboxylic-acid [COAAA].

11. The method according to claim 1, in which the compound of formula (I) is

AEOAA

4α,6α-dimethyl-2-oxo-hexadecahydro-indeno[5,4-f]quinoline-7-carboxylic-(2-amino-ethyl)-amide hydrochloride [AEOAA].

* * * * *